(12) United States Patent
Sakuma

(10) Patent No.: US 9,101,554 B2
(45) Date of Patent: Aug. 11, 2015

(54) SPRAY COMPOSITION FOR COMPANION ANIMAL BODIES

(71) Applicant: Eiji Sakuma, Tokyo (JP)

(72) Inventor: Eiji Sakuma, Tokyo (JP)

( * ) Notice: Subject to any disclaimer, the term of this patent is extended or adjusted under 35 U.S.C. 154(b) by 0 days.

(21) Appl. No.: 14/400,910

(22) PCT Filed: Apr. 25, 2013

(86) PCT No.: PCT/JP2013/062155
§ 371 (c)(1),
(2) Date: Nov. 13, 2014

(87) PCT Pub. No.: WO2013/172168
PCT Pub. Date: Nov. 21, 2013

(65) Prior Publication Data
US 2015/0125414 A1 May 7, 2015

(30) Foreign Application Priority Data

May 17, 2012 (JP) ................................. 2012-126512
Aug. 10, 2012 (JP) ................................. 2012-186977
Jan. 25, 2013 (JP) ................................. 2013-011803

(51) Int. Cl.
| | |
|---|---|
| A61K 8/97 | (2006.01) |
| A61K 8/39 | (2006.01) |
| A61K 8/42 | (2006.01) |
| A61K 8/44 | (2006.01) |
| A61K 8/86 | (2006.01) |
| A61K 8/49 | (2006.01) |
| A61K 8/67 | (2006.01) |
| A61K 8/92 | (2006.01) |
| A61K 8/891 | (2006.01) |
| A61K 36/53 | (2006.01) |
| A61K 36/82 | (2006.01) |
| A61Q 19/00 | (2006.01) |
| A61Q 5/00 | (2006.01) |
| A61Q 7/00 | (2006.01) |

(52) U.S. Cl.
CPC ... *A61K 8/97* (2013.01); *A61K 8/39* (2013.01); *A61K 8/42* (2013.01); *A61K 8/44* (2013.01); *A61K 8/4913* (2013.01); *A61K 8/673* (2013.01); *A61K 8/86* (2013.01); *A61K 8/891* (2013.01); *A61K 8/922* (2013.01); *A61K 8/925* (2013.01); *A61K 36/53* (2013.01); *A61K 36/82* (2013.01); *A61Q 5/00* (2013.01); *A61Q 7/00* (2013.01); *A61Q 19/00* (2013.01)

(58) Field of Classification Search
CPC ............. A61K 8/39; A61K 8/42; A61K 8/44; A61K 8/673; A61K 8/86; A61K 8/891; A61K 8/922; A61K 8/925; A61K 8/97
See application file for complete search history.

(56) References Cited

U.S. PATENT DOCUMENTS

| | | |
|---|---|---|
| 2003/0143172 A1 | 7/2003 | Ito et al. |
| 2004/0122109 A1 | 6/2004 | Fujii et al. |
| 2011/0008401 A1 | 1/2011 | Ranade et al. |

FOREIGN PATENT DOCUMENTS

| | | |
|---|---|---|
| JP | H06-240579 A | 8/1994 |
| JP | 2002-212037 A | 7/2002 |
| JP | 2002-332217 A | 11/2002 |
| JP | 2007-31346 A | 2/2007 |
| JP | 2007-217295 A | 8/2007 |
| JP | 2008-255028 A | 10/2008 |
| JP | 2011-513407 A | 4/2011 |
| WO | 02/055041 A2 | 7/2002 |
| WO | 02/100359 A1 | 12/2002 |
| WO | 2009/111128 A1 | 9/2009 |
| WO | 2010/055833 A1 | 5/2010 |

OTHER PUBLICATIONS

English machine translation of JP 2008-255028; Accessed Jun. 2, 2015.*
PCT, "International Search Report for International Application No. PCT/JP2013/062155."

* cited by examiner

*Primary Examiner* — Rachael E Bredefeld
(74) *Attorney, Agent, or Firm* — Manabu Kanesaka

(57) ABSTRACT

A spray composition for companion animal bodies includes a polyoxyethylene fatty acid ester, a polyoxyethylene alkyl ether, a silicone derivative, pantothenic acid, panthenol, PCA-Na, glutamic acid, a rice bran oil or a squalane oil or a camellia oil or a component containing a mixture of rice bran oil and squalane oil and camellia oil, a tea leaf extract or a tea flower extract or a component containing a mixture of tea leaf extract and tea flower extract, a rosemary extract or a rosemary leaf extract or a component containing a mixture of rosemary extract and rosemary leaf extract.

4 Claims, No Drawings

SPRAY COMPOSITION FOR COMPANION ANIMAL BODIES

RELATED APPLICATIONS

The present application is a National Phase Application of International Application No. PCT/JP2013/062155, filed on Apr. 25, 2013, which claims priorities from Japanese Application No. 2012-126512, filed on May 17, 2012, No. 2012-186977, filed on Aug. 10, 2012, and No. 2013-011803, filed on Jan. 25, 2013.

TECHNICAL FIELD

The present invention relates to a composition for companion animal bodies to be provided for companion animals such as dogs and cats, and particularly relates to a spray composition for companion animal bodies having excellent portability.

BACKGROUND ART

In recent years, companion animals such as dogs and cats (hereinbelow, referred to as "pets") increasingly have been living indoors with humans as family members with a purpose of healing the human mind as well as being kept as watchdogs. Pets play a major role as an important partner that can serve also as a companion to talk to, especially for those living alone.

Incidentally, it is essential for pets to walk because walking is a moderate workout for them. Since it is necessary to walk pets routinely, walking is often conducted also on rainy or snowy days. Unfortunately, if a pet enters the room with its skin and hair wet or with splashes of mud left on the pet after walking on a rainy or snowy day, the room gets dirty. Thus, the entire body of the pet has to be washed off or wiped every time it returns home. Additionally, getting wet with rain or snow may be a causal factor of skin diseases.

CITATION LIST

Patent Literature

Patent Literature 1: Japanese Patent Laid-Open No. 2002-212037

SUMMARY OF INVENTION

Technical Problem

The only way to protect pets from soil and water so far has been to put rain gear on pets. However, rain gear for pets is highly bulky and is not suitable for being carried, for example, to prepare for sudden rainfall or snowfall during walking. Alternatively, since putting rain gear on pets is troublesome, such gear is supposed to be put on before starting of walking. When a pet owner tries in the course of walking, it is very troublesome for the owner to put rain gear on a pet. Thus, the gear is still unsuitable for "being carried" at all.

Incidentally, in the case of commercially available treatments for humans, a highly viscous treatment agent contained in a pump bottle is taken directly onto a palm and applied on the hair. Leave-in spray treatments are also commercially available. Such hair treatments for humans are mainly composed of components that adhere to the hair and adsorb on the surface and inside of the hair to thereby maintain the luster of the hair for a long period. Patent Literature 1 discloses the technique concerning hair protective agents, and particularly, in the paragraph "0054," describes conditioners or the like for pets.

However, conventional conditioners are not so effective to prevent wetting with water and splashes of mud caused by rain or snow, although having water repellency. Moreover, the conditioners have poor portability as well as poor ease of use.

In view of such problems and the like, an object of the present invention is to provide a spray composition for companion animal bodies that has excellent soil- and water-proof action and has good portability and ease of use.

Solution to Problem

The spray composition for companion animal bodies of the present invention is a spray composition for companion animal bodies comprising a polyoxyethylene fatty acid ester, a polyoxyethylene alkyl ether, a silicone derivative, pantothenic acid, panthenol, PCA-Na, glutamic acid, a rice bran oil or a squalane oil or a camellia oil or a component containing a mixture of rice bran oil and squalane oil and camellia oil, a tea leaf extract or a tea flower extract or a component containing a mixture of tea leaf extract and tea flower extract, a rosemary extract or a rosemary leaf extract or a component containing a mixture of rosemary extract and rosemary leaf extract, based on the total amount of the composition for companion animal bodies, the content of the polyoxyethylene fatty acid ester is 10% by weight, the content of the polyoxyethylene alkyl ether is 10% by weight, the content of the silicone derivative is 52% by weight, the content of the pantothenic acid is 5% by weight, the content of the panthenol is 3.0% by weight, the content of the PCA-Na is 3.0% by weight, the content of the glutamic acid is 3.0% by weight, the content of the rice bran oil or the squalane oil or the camellia oil or the component containing a mixture of rice bran oil and squalane oil and camellia oil is 10% by weight, the content of the tea leaf extract or the tea flower extract or the component containing a mixture of tea leaf extract and tea flower extract is 3.0% by weight, and the content of the rosemary extract or the rosemary leaf extract or the component containing a mixture of rosemary extract and rosemary leaf extract is 1.0% by weight.

This makes it possible to provide a spray composition for companion animal bodies having excellent soil- and water-proof action. Additionally, since the composition is in a form of spray, it has excellent portability and ease of use and is easily adaptable to unexpected rainfall or snowfall in the course of walking, for example.

The viscosity of each of the polyoxyethylene fatty acid ester, the polyoxyethylene alkyl ether, the silicone derivative, and the pantothenic acid may be 5 cP or less.

The silicone derivative may be cyclopentasiloxane.

Advantageous Effects of Invention

The spray composition for companion animal bodies of the present invention makes it possible to provide a spray composition for companion animal bodies having excellent soil- and water-proof action. Additionally, since the composition is in a form of spray, it has excellent portability and ease of use and is easily adaptable to unexpected rainfall or snowfall in the course of walking, for example.

DESCRIPTION OF EMBODIMENTS

The spray composition for companion animal bodies of the present invention is composed of a mixture containing a silicone derivative. Specifically, the spray composition for companion animal bodies is characterized by containing a polyoxyethylene fatty acid ester (A), a polyoxyethylene alkyl ether (B), a silicone derivative (C), pantothenic acid (D), panthenol (E), PCA-Na (F), glutamic acid (G), a vegetable oil (H), an oil-soluble plant extract (I), and rosemary-derived component (J). Having such a constitution, the spray composition for companion animal bodies of the present invention can be easily sprayed on companion animals such as dogs and cats (hereinbelow, simply referred to as "pets") to thereby exhibit a water- and soil-proof effect on the entire body surface of the pets (that is, the hair and epidermis). Additionally, use of low-viscous components provides excellent atomizing performance and reduces clogging upon spraying.

A polyoxyethylene fatty acid ester (A) has an effect of preventing hair loss.

A polyoxyethylene alkyl ether (B) has an ultraviolet absorbing action, high affinity to the skin, and excellent dispersibility.

A silicone derivative (C) exhibits no penetration into the hair, has an effect of helping film formation, and has excellent volatility and water resistance. The silicone derivative also has an effect of improving the feel to thereby impart a dry feel and achieve a smooth touch. It should be noted that the conventional known silicone derivatives relatively often have a high viscosity, and thus, are not suitable for spraying. As silicone derivatives to be employed for the present invention, silicone derivatives having a relatively low viscosity are preferably employed. Specifically, cyclopentasiloxane is suitable.

Pantothenic acid (D) has an effect of promoting growth of the hair.

Panthenol (E), which is a component derived from fermented beans and egg yolk, has actions of promoting growth of the hair and of activating the skin cells.

PCA-Na (sodium pyrrolidone carboxylate solution) (F), which is a component derived from sugar cane and corn, achieves effects of moisturizing the skin surface and of enhancing flexibility and elasticity of the skin. The sodium pyrrolidone carboxylate solution is one of natural moisturizing factors (NMFs) that reside in the skin stratum corneum.

Glutamic acid (G), which is a component derived from palm oil and is an acidic polar side-chain amino acid, has poor water solubility, and achieves effects of moisturizing, of enhancing metabolism of the stratum corneum, and of preventing drying and maintaining healthy skin.

A vegetable oil (H) is, for example, rice bran oil, which is a liquid oil derived from rice bran and containing components such as triglyceride and glycosphingolipid obtained from rice bran of a gramineous plant "rice." It has an effect of preventing the skin from drying and roughness and imparting flexibility. Squalane oil and camellia oil may be employed as a vegetable oil. Furthermore, a component containing a mixture of rice bran oil, squalane oil, and camellia oil may be employed as a vegetable oil.

As an oil-soluble plant extract (I), for example, tea leaf extract, which is a component extracted from tea leaf stems and tea leaves, may be employed. The tea leaf extract contains components such as catechin tannin, caffeine, amino acids, and vitamin C. The tea leaf extract has moisturizing and antimicrobial actions and achieves an effect of keeping the skin healthy. Tea flower extract may be employed as an oil-soluble plant extract. Furthermore, a component containing a mixture of tea leaf extract and tea flower extract may be employed as an oil-soluble plant extract.

A rosemary-derived component (J) is derived from a plant called *Rosmarinus officinalis*, is rosemary extract or rosemary leaf extract extracted from leaves or blossoms of a Lamiaceae evergreen shrub "*Rosmarinus officinalis*," and contains components such as essential oils, flavonoid, and tannin. The rosemary-derived component has blood circulation promoting action, antioxidant action, action of suppressing melanin production, antibacterial action, anti-inflammatory action, action of suppressing stimuli, and cleaning action, and has effects of preventing hair loss and suppressing dandruff.

As a polyoxyethylene fatty acid ester (A), a polyoxyethylene alkyl ether (B), a silicone derivative (C), and pantothenic acid (D), low-viscous components are preferably employed for spraying. Specifically, a viscosity of 5 cP (centipoise) (a Brookfield type viscometer) or less is preferred. These components (A) to (D) have good compatibility with other components. Having a low viscosity and a low surface tension, the components also have excellent spreadability on the hair, a dry feel, and an effect of reducing the stickiness feel due to rain and snow. Particularly, even if a pet has got wet with rain after spraying, combing is satisfactory. Brushing also facilitates volatilization to thereby prevent oil contents from remaining on the hair. Additionally, these components have a low latent heat of evaporation and provide a slightly cool feeling, enabling the pet itself to live comfortably.

A suitable formulation example of the spray composition for companion animal bodies of the present invention is shown below. The contents below are based on the total amount of the composition. It should be noted that the present invention is not limited to the following formulation.

| | |
|---|---|
| Polyoxyethylene fatty acid ester (A) | 0.05 to 10% by weight |
| Polyoxyethylene alkyl ether (B) | 0.05 to 10% by weight |
| Silicone derivative (C) | 1.0 to 98.83% by weight |
| Pantothenic acid (D) | 0.01 to 5% by weight |
| Panthenol (E) | 0.01 to 3.0% by weight |
| PCA-Na (F) | 0.01 to 3.0% by weight |
| Glutamic acid (G) | 0.01 to 3.0% by weight |
| Vegetable oil (H) | 0.01 to 10% by weight |
| Oil-soluble plant extract (I) | 0.01 to 3.0% by weight |
| Rosemary-derived compontent (J) | 0.01 to 1.0% by weight |

This makes it possible to provide a spray composition for companion animal bodies having excellent soil- and water-proof action. Additionally, since the composition is in a form of spray, it has excellent portability and ease of use and is easily adaptable to unexpected rainfall or snowfall in the course of walking, for example.

More suitably, it is preferred to add 10% by weight to 52% by weight of the silicone derivative (C).

The most suitable formulation example of the spray composition for companion animal bodies is shown below.

| | |
|---|---|
| Polyoxyethylene fatty acid ester (A) | 10% by weight |
| Polyoxyethylene alkyl ether (B) | 10% by weight |
| Silicone derivative (C) | 52% by weight |
| Pantothenic acid (D) | 5% by weight |
| Panthenol (E) | 3.0% by weight |
| PCA-Na (F) | 3.0% by weight |
| Glutamic acid (G) | 3.0% by weight |
| Vegetable oil (H) | 10% by weight |
| Oil-soluble plant extract (I) | 3.0% by weight |
| Rosemary-derived component (J) | 1.0% by weight |

The most suitable formulation example is particularly mainly based on the silicone derivative (C), which is a component adhering to and forming a film on the hair surface of pets to thereby repel rain and snow water droplets, enhancing the soil- and water-proof effect.

A suitable method for producing the spray composition for companion animal bodies of the present invention is shown below. It should be noted that the present invention is not limited to the following production method. The ambient environmental temperature is normal temperature (for example, from 10 to 25 degrees).

<Step 1>: Into a cleaned first mixing tank, a polyoxyethylene fatty acid ester (A), a polyoxyethylene alkyl ether (B), a silicone derivative (C), and pantothenic acid (D) are charged and stirred. The stirring time is preferably one hour or more.

<Step 2>: Into a cleaned second mixing tank, panthenol (E), PCA-Na (F), glutamic acid (G), rice bran oil as a vegetable oil (H), tea leaf extract as an oil-soluble plant extract (I), and rosemary extract as a rosemary-derived component (J) are charged and stirred. The stirring time is preferably one hour or more.

<Step 3>: Into the first mixing tank, the mixture stirred in Step 2 is added and further mixed and stirred until dissolution to thereby obtain a composition for companion animal bodies. The stirring time is preferably one hour or more.

<Step 4>: The composition for companion animal bodies completed in Step 3 is filled into a mist spray container to thereby obtain a spray composition for companion animal bodies. It should be noted that an amount to be sprayed per use is preferably adjusted to from 0.2 ml to 0.5 ml.

As spray containers to be used, the known spray containers, such as triggered spray containers and dispensing pump spray containers may be employed. It should be noted that the viscosity of the components (A) to (D) may be from 1 to 10000 cP (centipoise) in the case where an aerosol spray container is used. However, an aerosol spray container may cause pets to sense an unpleasant cold feeling on spraying. Additionally, necessity of filling such containers with gases, such as propane gas and nitrogen increases risk. Use of triggered spray containers and dispensing pump spray containers can reduce a cold feeling which pets may sense. Use of low-viscous components having a viscosity of 5 cP or less as the components (A) to (D) can achieve an effect of maintaining a good injection condition until all the composition in the container is injected, even in the case of employing a pump spray container.

In the case of walking in rain and snow, the composition is sprayed on a pet directly from the spray container. The hair of the pet is covered with the composition for companion animal bodies. The composition having repelling action achieves a soil- and water-proof effect. It should be noted that the composition may be left as is after the owner and the pet get home because the composition contains no components deleterious to pets. Water droplets repelled on the hair may be simply wiped with a towel.

As described above, the spray composition for companion animal bodies of the present invention makes it possible to provide a spray composition for companion animal bodies having excellent soil- and water-proof action on the entire body surface of pets (that is, the hair and epidermis). Additionally, since the composition is in a form of spray, it has excellent portability and ease of use and is easily adaptable to unexpected rainfall or snowfall in the course of walking, for example.

Components having an anti-ultraviolet effect, such as arbutin components having a whitening effect, such as tranexamic acid, and the like may be added to and used in the spray composition for companion animal bodies of the present invention.

The invention claimed is:

1. A spray composition for companion animal bodies comprising i.) a polyoxyethylene fatty acid ester, ii.) a polyoxyethylene alkyl ether, iii.) a silicone derivative, iv.) pantothenic acid, v.) panthenol, vi.) sodium pyrrolidone carboxylate (PCA-Na), vii.) glutamic acid, viii.) a rice bran oil or a squalane oil or a camellia oil or a component containing a mixture of rice bran oil and squalane oil and camellia oil, ix.) a tea leaf extract or a tea flower extract or a component containing a mixture of tea leaf extract and tea flower extract, and x.) a rosemary extract or a rosemary leaf extract or a component containing a mixture of rosemary extract and rosemary leaf extract, wherein, based on the total amount of the composition for companion animal bodies, the content of the polyoxyethylene fatty acid ester is 10% by weight, the content of the polyoxyethylene alkyl ether is 10% by weight, the content of the silicone derivative is 52% by weight, the content of the pantothenic acid is 5% by weight, the content of the panthenol is 3.0% by weight, the content of the PCA-Na is 3.0% by weight, the content of the glutamic acid is 3.0% by weight, the content of the rice bran oil or the squalane oil or the camellia oil or the component containing a mixture of rice bran oil and squalane oil and camellia oil is 10% by weight, the content of the tea leaf extract or the tea flower extract or the component containing a mixture of tea leaf extract and tea flower extract is 3.0% by weight, and the content of the rosemary extract or the rosemary leaf extract or the component containing a mixture of rosemary extract and rosemary leaf extract is 1.0% by weight.

2. The spray composition for companion animal bodies according to claim 1, wherein the viscosity of each of the polyoxyethylene fatty acid ester, the polyoxyethylene alkyl ether, the silicone derivative, and the pantothenic acid is 5 cP or less.

3. The spray composition for companion animal bodies according to claim 1, wherein the silicone derivative is cyclopentasiloxane.

4. The spray composition for companion animal bodies according to claim 2, wherein the silicone derivative is cyclopentasiloxane.

* * * * *